United States Patent [19]

Clement et al.

[11] 4,328,250

[45] May 4, 1982

[54] ACTIVE DRIED BAKERS' YEAST

[75] Inventors: Philippe Clément, Roubaix; Jean-Paul Rossi, Marcq en Baroeul, both of France

[73] Assignee: Societe Industrielle Lesaffre, Paris, France

[21] Appl. No.: 930,163

[22] Filed: Aug. 2, 1978

Related U.S. Application Data

[63] Continuation of Ser. No. 702,019, Jul. 2, 1976, abandoned.

[30] Foreign Application Priority Data

Jul. 3, 1975 [FR] France .............................. 75 20943

[51] Int. Cl.$^3$ ...................... A21D 2/00; C12C 11/16; C12C 11/18; C12N 1/18
[52] U.S. Cl. ....................................... 426/18; 426/60; 426/62; 435/245; 435/256; 435/260
[58] Field of Search ............................ 426/18, 60, 62; 435/256, 245, 260

[56] References Cited

U.S. PATENT DOCUMENTS

| | | | |
|---|---|---|---|
| 1,727,847 | 9/1929 | White | 435/245 |
| 3,120,473 | 2/1964 | Deloffre | 435/256 |
| 3,617,306 | 11/1971 | Pomper et al. | 435/256 |
| 3,830,938 | 8/1974 | Morikawa et al. | 426/18 |
| 3,993,783 | 11/1976 | Langejan et al. | 424/62 X |

FOREIGN PATENT DOCUMENTS 1262648  2/1972  United Kingdom .

OTHER PUBLICATIONS

Reed, et al., Yeast Technology, The Avi Publ. Co., Inc., Westport, Conn., 1973, (pp. 21, 85, 96 & 150).

*Primary Examiner*—David M. Naff
*Attorney, Agent, or Firm*—Cushman, Darby & Cushman

[57] ABSTRACT

A dry yeast composition in particulate form containing at least 92% dry matter is prepared consisting essentially of active dry bakers' yeast capable of fermenting sweetened doughs containing more than 5% sugar and an emulsifying agent having an HLB value of between 3 and 11. The emulsifying agent is added to the yeast before drying and protects the yeast during drying.

23 Claims, No Drawings

ACTIVE DRIED BAKERS' YEAST

This application is a continuation application of U.S. application Ser. No. 702,019 filed July 2, 1976, and now abandoned.

The subject of the invention is a new active dried yeast for bread-making.

Its subject is also means for obtaining this dried yeast, that is to say a series of manufacturing processes and strains which can be used for this purpose.

The interest in active dried yeasts for bread-making, which are characterised by a dry-matter content equal to or greater than 92%, lies in the fact that their activity lasts for a long time, even at relatively high temperatures. Their disadvantage lies in the fact that drying causes them to lose a fairly large part of their initial fermenting activity and that, consequently, their activity on an equal dry-matter basis will always be weaker than that of initially fresh yeasts.

It is fitting to recall here that initially fresh yeasts are generally classified into two categories, those which come from so-called "slow" strains and those which come from so-called "quick" strains. Theis distinctive characteristic is their activity upon non-sweetened doughs and upon sweetened doughs (that is to say doughs containing in their composition saccharose or saccharose and glucose).

The first of these have a weak activity upon dough without sugar (saccharose), but they have considerable activity upon sweetened dough, that is to say they are very "osmotolerant". These strains, in general, reach their optimum fermenting activity at low nitrogen and $P_2O_5$ contents (N/D.M. 32 7 to 7.5 and $P_2O_5$/D.M. =2, with D.M. = dry matter).

The others have a very strong activity upon dough without sugar, but this diminishes rapidly in the presence of increasingly more sweetened doughs; they are not very osmotolerant. These strains, which are generally adapted to maltose fermentation, reach their optimum activity at high nitrogen and $P_2O_5$ contents (N/D.M = 8 to 8.5 and $P_2O_5$/D.M. = 2.5 to 3.5).

That called optimum composition is the composition for which a larger nitrogen or $P_2O_5$ content gives no more than a slight gain in activity and corresponds specially to a definite deterioration in the stability of the yeast obtained.

Until now, research workers applied themselves to producing dried yeasts having strong activity upon doughs with no or not very much sugar.

On the other hand, the problem of obtaining dried yeasts having strong activity upon doughs containing more than 5% of sugar did not arise and, consequently, there are not, at present, any dried yeasts on the market, having good fermenting activity upon sweetened dough.

This situation is exlained by the fact that the property of osmotolerance is much more affected by drying than the activity of the yeast upon dough without sugar. In other words, the loss of activity in drying is much greater when it is measured upon doughs containing at least 5% of sugar than when it is measured upon dough without sugar. It is recalled, in this respect, that the word "osmotolerance" derives from the hypothesis that yeasts vary in their sensitivity to the osmotic pressure created by the sugar added to the dough.

It has been established that the deterioration in the osmotolerance of the yeasts in drying is the greater as the osmotolerance is initially greater; this deterioration can, perhaps, be explained by the observation according to which it is the systems which permit the passage of sugars through the membrane, which are the most changed in the course of drying, whichever this may be.

This being so, it so happens that the regions, in which large amounts of leavened, well sweetened dough are consumed, are numerous, and consequently, the need for dried yeasts for use in such doughs is great.

The Applicant Company has therefore sought to perfect a dried yeast which is very active upon sweetened dough, this dried yeast preferably also having good activity upon dough without sugar and especially upon slightly sweetened dough.

Consequently, knowing that the reproducible tests used by the Applicant Company to measure the activity of a yeast are as follows:

Test A

Measurement of the gas released, after mixing with water, using BURROWS' and HARRISON's fermentometer (described in the Journal of the Institute of Brewing, vol. LXV no. 1, January—February 1959), Test $A_1$ (fresh compressed yeasts)

To 20 g of flour incubated at 30° C., there is added a weight of compressed yeast corresponding to 160 mg of dry matter, this yeast being mixed in 15 ml of water containing 27 g of NaCl per liter and 4 g of $SO_4(NH_4)_2$ per liter; this is kneaded for 40 seconds, using a spatula, so as to obtain a dough which is placed in a water bath set at 30° C.; thirteen minutes after the kneading was begun, the receptacle containing the dough is hermetically closed; the total amount of gas produced is measured after 60, then 120 minutes; this amount is expressed in ml at 30° C. and under 760 mm of Hg, Test $A'_1$ (dried yeasts)

Similar to Test $A_1$, but prior to kneading, the dried yeast is reconstituted in distilled water at 38° C.; for this purpose 40% of the volume of hydration water employed are used; the water complement, mixed with 405 mg of NaCl, is added to the product resulting from the fifteen minutes' reconstitution, Test $A_2$ (fresh compressed yeasts)

Test similar to Test $A_1$, but 100 mg of saccharose are added to the flour; the total amount of gas produced is measured after 60 minutes, Test $A'_2$ (dried yeasts)

Test identical to Test $A'_1$, but 100 mg of saccharose are added to the flour; the total amount of gas produced is measured after 60 minutes, Test $A_3$ (fresh compressed yeasts)

Test identical to Test $A_1$, but 2 g of saccharose are added to the flour; the total amount of gas produced is measured after 60 minutes, Test $A'_3$ (dried yeasts)

Test identical to Test $A'_1$, but 2 g of saccharose are added to the flour; the total amount of gas produced is measured after 60 minutes, Test $A_4$ (fresh compressed yeasts)

Test identical to Test $A_1$, but 5.5 g of saccharose are added to the flour; the total amount of gas produced is measured after 60 minutes, Test $A'_4$ (dried yeasts)

Test identical to Test $A'_1$, but 5.5 g of saccharose are added to the flour; the total amount of gas produced is measured after 60 minutes, and that the preliminary trials used by the Applicant Company are as follows:

Test B

Measurement of the gas released, with a CHOPIN zymotachygraph, manufactured by M. CHOPIN & Cie, 5 Rue Escudier, Boulogne-sur-Seine, France, Test $B_1$ (fresh compressed yeasts and instant dried yeasts not requiring previous reconstitution)

To 250 g of flour there is added a weight of compressed yeast or instant dried yeast corresponding to 1.6 g of yeast dry-matter, and 150 ml of salt water (50 g of salt/1.5 l of water); the mixture is kneaded for 6 minutes; the temperature of the dough must be 27° C. at the end of the kneading; the dough is placed in the apparatus and 6 minutes, measured exactly, after the kneading, the thermostatic chamber is put under pressure at 27° C.; the total release of gas recorded on a graph is measured, in ml, after 1 hour and 3 hours, Test $B'_1$ (dried yeasts which have to be reconstituted)

Test identical to Test $B_1$, but prior to the kneading, the dried yeast is reconstituted in distilled water at 38° C. (50 ml) for 15 minutes; the water and salt complement is added to the product of the 15 minutes' reconstitution, Test $B_2$ (fresh compressed yeasts and instant dried yeasts)

Test identical to Test $B_1$, but there are added to the flour 5% of sugar, 5% of margarine and 4.0 g of yeast dry-matter; after kneading, 250 g of dough are taken and introduced into the apparatus; the total amount of gas released is measured after 1 hour and 1 hour 30 minutes, Test $B'_2$ (non-instant dried yeasts)

Test identical to Test $B_2$, but, prior to kneading, the dried yeast is reconstituted in 50 ml of distilled water at 38° C. for 15 minutes; the water and salt complement is added to the product of the 15 minutes reconstitution;

the invention aims at producing, as a new industrial product, a dried yeast giving the following results:

Gas released greater than or equal to 44 ml in test $A'_3$,

Gas released greater than or equal to 20 ml, and preferably between 23 and 37 ml in test $A'_4$ and, preferably, Gas released greater than or equal to 39 ml in one hour, greater than or equal to 56 ml during the second hour and greater than or equal to 95 ml for the whole of the 2 hours in test $A'_1$.

According to a preferred method of realisation, the above-mentioned yeast gives rise to a release of gas of between 45 and 54 ml in test $A'_3$, and, preferably, between 47 and 54 ml in test $A'_3$.

The whole of these results shows that the dried yeast according to the invention gives, with respect to sweetened dough, results clearly superior to those of all the known dried yeasts; the preferred yeast gives in addition, with respect to dough without sugar, results comparable to the best dried yeasts sold until now.

The process which the Applicant Company has perfected, for preparing the above-mentioned dried yeasts, having a dry-matter content greater than 92%, preferably between 94 and 97%, is characterised by the fact that there is subjected to careful drying—that is to say to particularly gentle drying—a fresh, compressed osmotolerant yeast, containing 30–35% of dry matter, to which has been added an emulsion of an emulsifying agent having an HLB (Hydrophilic-Lipophilic-Balance) value between 3 and 11 in water, obtained by cultivating strains of yeast which are stable to drying, the cultivation conditions, which can include a discontinuous flow of molasses and/or an acid treatment carried out on the yeast cream, being such that the amount of buds on the yeast obtained is less than 5% and, preferably, less than 1%, the amount of proteins in the yeast obtained corresponds to the optimum activity of the cultivated strain, and, in addition, the composition of the fresh compressed yeast satisfies the following inequalities:

trehalose/dry matter $\geq 12\%$ $2.3 \leq$ nitrogen/$P_2O_5 \leq 3.8$ cryoscopic lowering of the water outside the yeast below 0.5° C.

It is pointed out that, in order to measure the cryoscopic lowering of the water outside a compressed yeast containing 30–35% of dry matter, a cream is made with 100 g of the compressed yeast and 30 g of completely demineralised water, this cream is centrifuged and the cryoscopic lowering of the supernatant liquid obtained is measured, for example using a cryoscope of the BECKMAN type (PROLABO no. 0329 600). The lowering of the freezing point measured is proportional to the amount of gram molecules of substances dissolved in the water outside.

The Applicant Company has found that particularly satisfactory results were obtained when the strain used within the scope of the above-mentioned process was a distillers' yeast which was slow, very osmotolerant and stable to drying, such as that which was deposited at the N.C.Y.C. (National Collection of Yeast Cultures, Agricultural Research Council's Food Institute, Colney Land, Norwich, Norfolk NR4 7UA, England), under number R 30, or one of the hybrids which it obtained by cross-breeding and successive selection, carried out with the aim of obtaining strains which are both quick and osmotolerant, and which are deposited at the N.C.Y.C. under numbers R 37 and R 38.

The invention also aims at providing the abovementioned strain and hybrids as new industrial products.

The three strains R 30, R 37 and R 38 are saccharomyces cerevisiae. In the standard taxonomic tests carried out by the N.C.Y.C., according to the work by J. LODDER, The Yeasts, A Taxonomic Study, 1970, they are distinguished essentially by the following characteristics, assembled in table I.

TABLE I

| Tests | R 30 | R 37 | R 38 |
|---|---|---|---|
| Assimilation of the sugars | | | |
| Trehalose | + | + | − |
| Melezitose | + | + slight latent | − |
| α-methylglucoside | + | + latent | − |
| Fermentation of the sugars | | | |
| Galactose | + 3 weeks | + 24 hours | + 2 weeks |
| Increase in medium without vitamins | − | − | ∓ |
| Sporulation on potassium acetate | 1 to 2 spores per ascus | 3 spores per ascus | 2 to 3 spores per ascus |

From the point of view of the biochemistry of the yeasts, these three strains are distinguished very little from one another, especially the isolated strain of yeast R 30 and the yeast hybrid R 37, but the technological characteristics of these two strains are very different. The taxonomic tests are of little value to distinguish the strains within the same species, all the more so since their reproducibility is uncertain. It is because of their very weak reproducibility that no test giving a description of the morphology of the yeasts is given.

Apart from the above-mentioned characteristics, the invention aims further at other characteristics which are made use of, preferably, at the same time and which will be mentioned more explicitly hereinafter.

And it can, in any case, be well understood using the rest of the description, which follows, and the accompanying examples, the said additional description and examples being given in keeping with preferred methods of carrying out the invention.

With the intention, consequently, of manufacturing a dried yeast of the type in question, having the characteristics of the yeasts according to the invention, one goes about it as follows or in an equivalent manner.

Firstly there is selected, according to the invention, a yeast strain stable to drying and capable of giving a fresh yeast having a release of gas of more than 45 in test $A_3$. Preferably, this yeast strain will be capable of giving a fresh yeast having a release of gas of more than 105 in test $A_1$ (for the whole of the 2 hours).

It is starting from the strain thus selected that the preparation of the fresh compressed yeast, which is subjected to drying, is carried out.

The preparation of the fresh compressed yeast comprises a series of treatments and cultivation stages according to the invention in question and which confer upon the latter the properties sought, which it keeps during drying, due both to the acquired fitness for drying and to the wisely selected characteristics of the latter.

During this series of treatments and of cultivation stages, the osmotolerant characteristics of the starting strain are increased and these characteristics are caused to be kept.

Thus it is that the invention permits there to be obtained, in an unexpected manner, dried osmotolerant yeasts having good activity upon very sweet dough, and enabling the amounts of yeast generally necessary for such doughs to be reduced. Thus it is that the invention also enables there to be obtained in an unexpected manner starting from a quick strain, a compressed yeast, then a dried yeast which is both osmotolerant and remarkably active upon dough without sugar.

In order to increase the osmotolerant characteristics of the starting yeast, it is possible to lower its invertase activity by chemical treatment of the yeast cream, for example by means of sulphuric or hydrochloric acid. Such treatment gives interesting results with respect to very sweet dough when the fresh yeast harvested has invertase activity greater than 30 units (the invertase unit being defined as the production of one micromole of reducing sugars over 5 minutes per mg of yeast dry matter at 30° C. and at pH 4.7 without plasmolysis of the yeast, or one demi-micromole of invert saccharose) and if this invertase activity can be lowered by short acid treatment at low temperature, bringing about only a slight change in the fermenting strength with respect to dough without sugar. The treatment can be carried out by acidifying the creamed yeast to a pH between 1.3 and 1.7 with a solution of dilute acid, followed by neutralisation to about pH 4.5. The temperature of the treatment is generally between 4° and 20° C. and the period of acid/yeast cream contact before neutralisation is generally between 5 and 60 minutes; these data must be determined experimentally so as to obtain a value of the invertase activity of the yeasts below 30, preferably between 5 and 20, without changing or by changing by less than 10% the gassing power of the yeasts with respect to dough without sugar.

As has been stated above, the influence of the invertase treatment of the yeast is marked only for the very sweet doughs and for the quick yeasts which are rich in invertase. For the not very or average sweet doughs (tests $A_3$ and $B_2$), it is of limited interest: the lowering of the invertase activity of the quick yeasts adapted to maltose and stable to drying which are known, does not enable dried yeasts having a release of gas of more than 45 ml in test $A'_3$ to be obtained; moreover its negative action upon the activity of dough without sugar is noted. It is only in test $A_4$ that this treatment, applied to a quick yeast which in very rich in invertase, shows a clear improvement.

In order to have yeasts which perform very well on sweetened doughs whatever their sugar content and whatever type of strain is used, it will be better to modify the method of propagating the yeast during cultivation, in particular by adopting a method of discontinuously feeding the yeasts in the last multiplying cycle.

The yeast is generally multiplied discontinuously in large vats, but feeding with molasses and with the different substances necessary for multiplying is always carried out continuously, according to an approximately exponential curve so as to contribute an amount of substrates proportional to the amount of yeast in the vat at each moment (constant amount of multiplication). In fact, the man skilled in the art causes this amount of multiplication and the proportion of the different substances of the nutrient mixture to vary in order to regulate the composition of the yeast obtained. Such a fermentation cycle lasts between 10 and 20 hours and the multiplication factor of the yeast mass is between 3 and 9.

The flow of molasses and of the other ingredients is always carried out continuously, for it has been shown for a long time that the concentration of sugar and nutrient substances in the culture medium had, at each moment, to be very low to obtain a maximum yield (cf. "Yeast Technology", by JOHN WHITE, 1954—page 58).

Now, the Applicant Company has made evident the fact that if, contrary to the above-mentioned universally-adopted practice, the yeast remainded in the presence, in the culture medium, of a large concentration of sugar, its osmotolerance, that is to say its capacity to ferment sweetened doughs, was clearly increased. This increase in osmotolerance is all the more marked since the instantaneous concentrations of sugar in the vat are stronger and the treatment is applied to the longer multiplication stages.

On a practical level, in order to carry out the process, it is sufficient, in the last multiplication cycle, to cause the molasses which have to be introduced in a given time to flow in over a much shorter period, the flow being interrupted during the remainder of this period. Thus, for a multiplication cycle of 12 hours, it is sufficient to run in, over for example 5 or 10 minutes at the beginning of each hour or of each half-hour, the amount of molasses which normally would have had to have been run in over the period of time comprising the inflow-time extended by the interval separating the end of this inflow from the commencement of the following inflow.

The discontinuous flow must be carried out for the final multiplication hours, before harvesting the yeast intended for drying. Preferably it will be carried out for at least the final 10 hours of discontinuous fermentation, corresponding to a multiplication factor of the cell mass fermenting, of at least 3.

This process is necessarily carried out discontinuously, that is to say within the scope of a process in which the yeast is not harvested continuously, but only at the end of a multiplication cycle of between 10 and 20 hours. In fact, within the scope of such a process, the yeast multiplying in the vat is put into the presence—at each instantaneous flow at regular intervals—of generally increasing concentrations of sugar, since the total flow of molasses over a given period is proportional to the quantity of yeast present in the vat.

Aeration of the fermentation vat is carried out according to the dissolved oxygen content present in the fermenting wort, in such a manner that excess air is not blown in, so as to avoid unnecessary drag out of the alcohol formed and so as to avoid too great reassimilation of the alcohol during the last two hours of fermentation with a view to maintaining a maximum trehalose content in the yeast. Preferably the amount of oxygen dissolved will be maintained between 2% (0.0046 mM $O_2$ liter) and 10% of the saturation.

Another advantage in the use of a discontinuous process with reference to a process including the continuous harvesting of the yeasts, is that within the scope of such a process, the loss in yield is minimum, for there is no loss of sugar (a part of which in a process with continuous harvesting and discontinuous flow of molasses would be dragged out with the permanently removed yeasted wort) and the largest part of the alcohol formed is reassimilated.

The amount of cell increase during the last 10 hours of fermentation and consequently the flow of molasses calculated over one hour, are selected in the same manner as in the discontinuous processes with continuous flow of molasses, in such a manner that there are obtained the composition sought of the yeast and an amount of budding in the harvested yeast as low as possible, less than 5%, in fact 1%, the remaining buds being, for the most part, fat buds ready to become detached.

With regard to the composition which fresh yeast derived from the last fermentation stage must have, the following conditions have to be complied with:

nitrogen content corresponding to the optimum activity, $$\frac{\text{trehalose content}}{\text{dry-matter content}} \geq 12\%$$

$$\frac{\text{nitrogen content}}{P_2O_5 \text{ content}} \text{ between 2.3 and 3.8}$$

In the case in which the process is used, which consists of causing the molasses to flow in a discontinuous manner at the end of the production of the yeast which will be dried, it is desirable that the dilution of the culture medium should be as slight as possible. This dilution can be characterised by the following ratio:

$$\frac{\text{weight of culture medium in the vat at the end of multiplication}}{\text{molasses poured into the vat during the multiplication cycle}}$$

which must be between 3 and 7, preferably between 3.8 and 5.

In all cases (possible acid treatment of the yeast cream, and possible use of the process with discontinuous flow), the yeast is washed with drinking water, in such a manner that the compressed yeast satisfies the condition according to which the cryoscopic lowering of the water outside the yeast is less than 0.5° C.

As mentioned above, the cryoscopic lowering of the water outside the yeast is proportional to the grammolecules of dissolved substances. These dissolved substances can have action which is really disastrous during drying.

It has been made evident that if the yeast contained a content of 0.5 g of NaCl per 100 g of yeast dry-matter resulting either from the acid treatment or from the use of the salt process to filter the yeast, as described in British Pat. No. 763,926, there is recorded with drying a loss of additional strength of 5% with regard to dough without sugar and of 8% with regard to sweetened dough.

The process consisting of causing the molasses to flow in a discontinuous manner has, amongst other results, that of greatly lowering the invertase content of the yeasts; however, this is not the only explanation of its action upon the osmotolerance, for, as has been seen, this lowering of invertase activity is of interest only when working very sweet doughs, whereas this process also improves the activity of the yeasts upon doughs having much a lower sugar content.

From the fact that it also lowers the invertase activity of the yeasts, it is generally not of interest to make a yeast cultivated with discontinuous flow of molasses, undergo acid treatment, except when a quick strain, having very high invertase activity produced with a view to fermenting doughs containing more than 15% of sugar with reference to the flour, is concerned.

In the case in which one of the three preferred strains mentioned above is employed, it is not essential to make provision for the two treatments mentioned above.

Strain N.C.Y.C. No. R30 is very osmotolerant and remains so after drying, if the conditions described above are fulfilled. With sweetened doughs it gives performances which are already very interesting. Without particular treatment, the fresh yeast obtained from this strain has low invertase activity, of the order of 30 units; it is not improved by acid treatment. On the other hand, its performances are improved by discontinuous cultivation with discontinuous flow of molasses, but the use of this relatively expensive process is not essential.

The N.C.Y.C. hybrids R37 and R38 are particularly interesting, for they enable, without special treatment and with the reservation of complying with the conditions described above, dried yeasts having performances with respect to sweetened doughs comparable to those of dried yeasts produced from modern hybrids of quick yeasts, cultivated discontinuously with discontinuous flow of molasses, to be obtained. Now, this treatment involving the discontinuous flow of the molasses is relatively expensive, since it involves an additional consumption of molasses of the order of 10 to 25%. The N.C.Y.C. hybrids R37 and R38 give fresh yeasts having invertase activity of the order of 60 to 70 units. When working very sweet doughs it is interesting to make them undergo acid treatment.

Having thus obtained—either starting from one of the three N.C.Y.C. strains nos. R30, R37 and R38, or starting from a fresh yeast subjected to acid treatment, or starting from a culture with discontinuous flow of molasses, or again by combining at least two of these three means—a fresh osmotolerant yeast which has the lowest possible amount of budding and which satisfies the four following conditions regarding its composition:
   amount of proteins corresponding to the optimum activity,
   trehalose content with respect to dry matter $\geq 12\%$
   $2.3 \leq$ nitrogen content/$P_2O_5$ content $\leq 3.8$
   cryoscopic lowering of the water outside the fresh yeast to 30–35% of dry matter below 0.5° centigrade,
it is subjected to particularly careful drying.

Flash (pneumatic conveyor) dryer, fluidised bed drying or a combination of these two methods of drying can be used.

This drying treatment is employed in the presence of emulsifying and stabilising agents having film-forming properties suitable for protecting the yeast during drying and for facilitating its reconstruction.

Thus, there can be added to the yeast an emulsion in water of sorbitol ester, or of lactic ester, or of diacetyl tartaric ester of mono and diglycerides, or of stearoyl 2 lactylate of sodium or calcium and of gum arabic, or of guar gum, or of carraghenate.

The content of emulsifying agents is calculated so as to represent 0.5 to 2% of the finished product, and that of the agent stabilising the emulsion 0.5% to 1% of the finished product.

Before the first drying phase, the fresh yeast, the dry-matter content of which is generally from 30 to 35%, is finely divided by extrusion through a grid having a mesh width of between 0.5 and 3 mm.

Pneumatic conveyor dryer is of interest to permit particularly brief drying.

The yeast is dried to at least 92% of dry matter, preferably to 94 to 97% of dry matter. The dry matter of the yeast obtained is controlled by blowing into the final compartment of the drying apparatus used, dehydrated air having a relative humidity which is in equilibrium with the dry matter desired for the yeast.

In order to prevent any beginning of oxidation of the yeast, which is harmful to its preservation, all the drying, or the final stages of drying, when for example the yeast has reached a dry matter content of 80%, can be carried out under vacuum or under inert gas such as, for example, nitrogen or carbon dioxide.

All the drying is preferably carried out continuously and is conducted in such a manner that the temperature of the yeast never reaches 35° C. Although that is not of prime importance, it is preferable for the total period of drying to be as short as possible. It must be less than 5 hours, and it will preferably be equal to or less that 1 hour.

The dried yeasts thus obtained can be incorporated in the dough either after reconstitution at 38° C., or immediately. Similar results are obtained for these dried yeasts in tests B and B'.

They are preferably conditioned under vacuum or under an inert atmosphere, in such a manner that the residual oxygen content is less than 2% of the volume of the conditioning restored to atmospheric pressure.

This being so, the invention is illustrated by the following examples.

EXAMPLE 1

Selection of the strains

For each strain to be tested, a 24-hour culture is made, with recourse to 3-liter fermentors (see Yeast Technology, J. WHITE, 1954—pages 103 to 106). The culture medium has a total volume of 1100 ml. The sugar is introduced in the form of molasses. The air is filtered on a membrane of the Millipore type at the rate of 1 m$^3$/hour for a battery of three fermentors. Innoculation is carried out with 300 mg of yeast obtained by anaerobic culture in flasks.

The strains R30, R37 and R38 were thus preselected. In Table II there are recorded the results obtained during a series of tests made with these three strains and with the hybrids (tests in parallel recorded on the last line) of quick yeast adapted to maltose and stable to drying.

TABLE II

| Strains tested | Results | | Invertase activity |
|---|---|---|---|
| | Test A$_1$ 1 hour | Test A$_3$ 1 hour | |
| Distiller' yeast N.C.Y.C. R 30 | 25 | 58 | 30 |
| Yeast hybrid N.C.Y.C. R37 | 35 | 58 | 60 |
| Yeast hybrid N.C.Y.C. R 38 | 33 | 66 | 70 |
| Hybrids of quick yeast adapted to maltose | 60 | 45–57 | 50–200 |

The yeasts harvested are very unstable. The results obtained do not correspond exactly to what can be obtained within the scope of the production of yeasts stable to drying, or of compressed commercial yeasts. They cannot be reproduced very exactly. The results obtained must always be evaluated with reference to one or two control strains.

EXAMPLE 2

Recourse is had to a battery of pilot fermentors constituted as follows:
   internal diameter 45 cm, height 85 cm, useful volume 80 l,
   double casing permitting regulation of the temperature of the fermenting wort,
   air inlet situated at the base of the vat, surmounted by an agitator rotating at 150 r.p.m. driven by a 3 HP motor,
   device for flow of the ingredients through distributing pumps of BRANN and LUBBE brand, having an hourly output which can be regulated between 0.1 liter/hour and 6 liters/hour,
   device for automatic regulation of the pH to a value as shown recorded, by inflow of dilute sulphuric acid, and
   device for regulating the height in the vat of the fermenting liquid by inflow of anti-foam agent.

In each test, the yeast is inoculated at hour 0 into the base of a 35-liters vat containing 160 g of molasses, 15 g of nitrogen and 15 g of P$_2$O$_5$. A fermentation test lasts 14 hours, at the end of which the yeast produced is harvested.

At the end of 14 hours, the weight of the vat is 63 kg (a little more than 60 liters) and the amount of molasses poured in is 13.1 kg containing 50% of Clerget sugar. The dilution of these tests is thus:

$$\frac{\text{weight of yeasted wort in the vat at the end of fermentation}}{\text{molasses poured in the vat}} = \frac{63}{13.1} = 4.8$$

The molasses is poured in continuously, in increasing amounts at each hour, except during the final hours.

Nitrogen is introduced in the form of ammonia in solution; it is also caused to flow in increasing amounts at each hour ("exponential" curve), this inflow being stopped at hour 12. Phosphorus is introduced in the form of phosphoric acid for 5 hours. The amounts of nitrogen and $P_2O_5$ introduced are calculated so as to obtain the desired composition taking as hypothesis a yield:

$$\frac{\text{yeast containing 30\% of dry matter}}{\text{molasses containing 50\% of Clerget sugar}} = 100$$

and an assimilation yield of $P_2O_5$ and mineral nitrogen plus nitrogen assimilable brought by the molasses, of 100.

The amount of air blown in is regulated as a function of the amount of alcohol in the vat.

The yeast is separated off and washed in a centrifuge, dehydrated to 32–33% of dry matter on a rotating filter under vacuum, employing the salt process (salt which is eliminated very carefully by inclined sprinklers on the rotating filter) and finally extruded either in 500 g blocks or in strands 0.6 mm in diameter.

Washing is carried out in such a manner that the cryoscopic lowering of the supernatant liquid obtained starting from a "cream" constituted by 100 g of yeast containing 30–35% of dry matter and removed on coming out of the filter and 30 g of demineralised water, is of 0.3° C.

To the yeast intended for drying, there is added a thin emulsion, constituted by sorbitol ester and gum arabic, at the rate, respectively, of 1.5% and 0.7% of the yeast dry-matter.

The yeast extruded into strands 0.6 mm in diameter is dried on a laboratory discontinuous fluidiser in 30 to 40 minutes, so that the temperature of the yeast does not exceed 35° C. during drying.

Great attention is paid to the fluidisation and to the beginning of the drying which must be quick and homogeneous. In order to do this, the yeast is vibrated manually at the beginning of drying.

At the end of the drying, dehydrated air containing 7 g of water per kg of air is blown in so that the yeast can be regulated to the desired dry matter.

The yeast obtained contains 94% of dry matter; it is presented in the form of small strands, 1 to 2 mm long, light cream in colour.

This record of tests enables the results obtained in fermentors of 3 liters total volume (culture medium 1.1 m) to be confirmed, and the stability to drying of the preselected strains to be tested.

This record of tests is applied to the three strains deposited at the N.C.Y.C. under numbers R30, R37 and R38, and to a hybrid of quick yeast, adapted to maltose and particularly stable to drying.

The inflow of nitrogen is calculated to obtain a yeast containing 7% of nitrogen with respect to dry matter with the N.C.Y.C. strain R30, and 8% of nitrogen with respect to dry matter with the three other strains.

The inflow of $P_2O_5$ is calculated to have a nitrogen/$P_2O_5$ ratio of 3.2.

The yields: $\frac{\text{yeast containing 30\% of } D.M.}{\text{molasses containing 50\% of Clerget sugar}}$ obtained for these four strains are between 95 and 100, without the differences obtained being significant. Consequently, the composition objectives aimed at are achieved.

The trehalose content with respect to yeast dry matter is above 13% and the cryoscopic lowering of the water outside the yeasts after passing over a rotating filter is below 0.3° C. The amount of budding of the yeasts obtained is 1%.

The results obtained for the yeasts containing 32–33% of dry matter and 94% of dry matter are recorded in the recapitulatory table III (lines 1 to 4).

EXAMPLE 3

The quick yeast hybrid already cultivated in example 2 and the N.C.Y.C. hybrid no R38 are cultivated according to the record of tests described in example 2. The yeast cream is taken to pH 1.4 with hydrochloric acid in normal solution. The treatment is stopped by neutralisation to pH 4.5 when the expressed yeast containing 30% of D.M. has no more invertase activity than 15, then the cream is filtered on a rotating filter under vacuum and treated as in the previous example.

The results obtained are recorded in the recapitulatory table III (lines 5 and 6).

EXAMPLE 4

Starting from the quick yeast hybrid already cultivated in examples 2 and 3 and starting from the N.C.Y.C. strain no R30, a fresh yeast and a dried yeast are produced, according to the record of tests described in example 2, but the inflow of molasses is carried out in a discontinuous manner, the molasses which have to flow in over 1 hour, being caused to flow in at the beginning of each hour for 10 minutes. Aeration is regulated as a function of the amount of dissolved oxygen. The inflow of nitrogen (taking into account the nitrogen assimilable brought by the molasses) and of $P_2O_5$ is reduced by 10% in order to take into account the fall in yield.

The yield of these tests expressed by the ratio:

$$\frac{\text{yeast containing 30\% of dry matter}}{\text{molasses containing 50\% of Clerget sugar}} \text{ is about 80\%.}$$

The amount of buds on the yeast obtained is 1%. The amount of trehalose with respect to dry matter is from 12 to 13%. The results of the fermenting activities measured on fresh yeast and on dried yeast are recorded in the recapitulatory table III (lines 7 and 8).

EXAMPLE 5

In the recapitulatory table III (lines 9 and 10) there appear the best results recorded with dried yeast samples in commerce:
- a dried yeast obtained with a slow strain, manufactured in North America (line 9)
- a dried yeast obtained with a quick strain, manufactured in Europe (line 10).

Measurement, with a CHOPIN zymotachygraph, of the gas released from by the dried yeast obtained with a slow strain, manufactured in North America, was carried out using test B' (B'$_1$ and B'$_2$); in fact, unlike all the other yeasts tested, this dried yeast, of American origin, gives results which are clearly inferior by directly incorporating the yeast into the dough.

TABLE I

| | FRESH COMPRESSED YEAST | | | | | | | | DRIED YEAST | | | | | | | |
|---|---|---|---|---|---|---|---|---|---|---|---|---|---|---|---|---|
| | | | | | Test $B_1$ | | Test $B_2$ | | | | | | Test $B_1$ | | Test $B_2$ | |
| | $A_1$ | $A_2$ | $A_3$ | $A_4$ | 1h | 3h | 1h | 1h30 | $A_1'$ | $A_2'$ | $A_3'$ | $A_4'$ | 1h | 3h | 1h | 1h30 |
| Distillers' yeast N.C.Y.C. No. R 30 (example 2) | 37+48=85 | 52 | 56 | 40 | 260 | 1200 | 520 | 900 | 32+43=75 | 45 | 47 | 32 | 230 | 1050 | 430 | 750 |
| Yeast hybrid N.C.Y.C. No. R 37 (example 2) | 45+66=111 | 55 | 56 | 24 | 310 | 1480 | 520 | 900 | 40+58=98 | 48 | 48 | 20 | 270 | 1300 | 430 | 750 |
| Yeast hybrid N.C.Y.C. No R 38 (example 2) | 45+64=109 | 54 | 58 | 24 | 300 | 1460 | 540 | 950 | 40+57=97 | 47 | 49 | 20 | 260 | 1300 | 450 | 790 |
| Hybrid of quick yeast adapted to maltose and stable to drying (example 2) | 55+80=135 | 59 | 49 | 22 | 350 | 1700 | 450 | 800 | 48+70=118 | 50 | 41 | 18 | 300 | 1500 | 380 | 680 |
| Quick yeast hybrid with acid treatment of the yeast cream (example 3) | 51+76=127 | 55 | 52 | 29 | 320 | 1600 | 480 | 870 | 44+66=110 | 47 | 44 | 24 | 280 | 1400 | 400 | 730 |
| Yeast hybrid N.C.Y.C. No. R 38 with acid treatment of the yeast cream (example 3) | 44+64=108 | 54 | 60 | 29 | 300 | 1450 | 550 | 980 | 39+56=95 | 46 | 50 | 24 | 260 | 1270 | 460 | 820 |
| Hybrid of quick yeast cultivated with discontinuous flow of molasses (example 4) | 54+79=133 | 60 | 59 | 28 | 340 | 1690 | 540 | 950 | 47+69=116 | 51 | 49 | 23 | 290 | 1500 | 450 | 800 |
| Distillers' yeast N.C.Y.C. No. R 30 cultivated with discontinuous flow of molasses (example 4) | 35+45=80 | 54 | 62 | 43 | 230 | 1060 | 580 | 1000 | 30+40=70 | 47 | 52 | 34 | 200 | 930 | 480 | 850 |
| Dried yeast obtained with a slow strain from North America (example) 5) | | | | | | | | | 34+38=72 | 42 | 32 | 14 | 200 | 930 | 240 | |
| Dried yeast obtained with a strain from Europe (example 5) | | | | | | | | | 48+70=118 | 50 | 40 | 17 | 280 | 1500 | 360 | |

Examination of these results shows:

that the fermentation of sweetened doughs leavened with the yeast, and especially very sweet doughs, poses specific problems, requiring special yeasts, and in particular that the tests on dough without sugar more generally carried out in order to measure the activity of the yeasts teaches very badly regarding the activity of the yeasts with respect to sweetened doughs;

that obtaining dried yeasts adapted to sweetened doughs is a problem which is all the more complex since the property of osmotolerance of the yeasts is greatly affected by drying;

the necessity to pose, in specific terms, the problem of obtaining dried yeasts adapted to sweetened doughs; and the technical progress achieved by the invention.

The invention also aims at providing, as new industrial products, products for bread-making containing sugar in their constituent formula and obtained using one of the dried yeasts described above or prepared by employing the processes described.

As goes without saying, and, moreover, as already appears from the foregoing, the invention is in no way limited to those of the methods of using it and carrying it out which have been more specifically considered; it includes, on the contrary, all modifications.

We claim:

1. A yeast composition in solid particulate form, consisting essentially of an active dry baker's yeast and an emulsifying agent having an HLB value of between 3 and 11 in water and in an amount sufficient to protect said yeast against deterioration during drying, said composition having a dry matter content of at least 92%, and having the capability of fermenting sweetened doughs containing more than 5% sugar, and wherein said composition (a) releases an amount of gas between 45 ml and 54 ml in test $A'_3$ wherein in said test $A'_3$ 160 mg of dry matter of said dry yeast is rehydrated with 6 ml of distilled water at 38° C. and at the end of 15 minutes of rehydration adding the amount of water, together with 405 mg of NaCl, required to bring the total to 15 ml, to the product resulting from the fifteen minutes rehydration and then adding the resulting yeast/salt/water composition to 20 g of flour, and 2 g of saccharose at 30° C., thereafter kneading the resulting mixture for 40 seconds to obtain a dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and also (b) releases an amount of gas between 23 and 37 ml in test A'$_4$ wherein in said test A'$_4$ the procedure of said test A'$_3$ is followed except that there is added to said flour 5.5 g of saccharose, and the total amount of gas produced is measured after 60 minutes.

2. A yeast composition according to claim 1, wherein said composition also releases an amount of gas equal to or greater than 39 ml after 60 minutes, and equal to or greater than 95 ml for the whole of the 120 minutes, in test A'$_1$ wherein in said test A'$_1$ 160 mg of dry matter of said dry yeast is rehydrated with 6 ml of distilled water at 38° C. and at the end of 15 minutes of rehydration adding the amount of water together with 405 mg of NaCl, required to bring the total to 15 ml to the product resulting from the fifteen minutes rehydration and then adding the resulting rehydrated yeast/salt/water composition to 20 g of flour at 30° C., thereafter kneading the resulting mixture for 40 seconds to obtain a dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes, and then after the expiration of 120 minutes.

3. A yeast composition according to claim 1, wherein said composition releases an amount of gas between 47 and 54 ml in said test A'$_3$.

4. A composition according to claim 2, wherein said composition releases an amount of gas between 47 and 54 ml in said test A'$_3$.

5. A composition according to any one of claims 1, 2, 3 or 4, wherein said emulsifying agent is present in a required amount of between 0.5% and 2% by weight.

6. A composition according to any one of claims 1, 2, 3 or 4, wherein said composition has a dry matter content between 94% and 97%.

7. A bread-making dough product containing at least 5% sugar in its constituent formula and an active dried baker's yeast composition according to claim 1.

8. A process for preparing a yeast composition in solid particulate form, consisting essentially of an active dry baker's yeast and an emulsifying agent having an HLB value of between 3 and 11 in water and in an amount sufficient to protect said yeast against deterioration during drying, said process comprising successively and in combination:

(1) selecting a yeast strain stable to drying and capable of giving a fresh compressed yeast having a gas release of at least 45 ml in test A$_3$, wherein said test A$_3$ consists in: adding to a mixture of 20 g of flour and 2 g of saccharose an amount of said yeast strain, corresponding to 160 mg of dry matter in 15 ml of water containing 27 g of NaCl and 4 g of $(NH_4)_2SO_4$ per liter, kneading the resulting yeast/flour/saccharose mixture for 40 seconds to obtain a dough, maintaining said dough at 30° C. in a vessel for 13 minutes after the beginning of said kneading, thereafter hermetically sealing said vessel, and measuring the total gas released therefrom at the end of 60 minutes;

(2) cultivating said yeast strain discontinuously in a plurality of multiplication cycles, having several hours duration each, and carried out in vats previously provided with inoculating yeast and water, by regulated inflows of molasses and other nutrients including nitrogen and $P_2O_5$, harvesting the yeast a the end of each multiplication cycle, and wherein during the last of said multiplication cycles, the cultivation conditions consist essentially in the combination of:

(i) discontinuous inflow of the molasses during the final hours of said last multiplication cycle before harvesting the yeast intended for drying, (ii) maintaining a value of between about 3 and about 7 for the weight ratio of (Culture medium)/(molasses)

wherein "(culture medium)" refers to the entire content of the culture vat including water, yeast and nutrient substances, calculated at the end of the last multiplication cycle and wherein "(molasses)" refers to the total quantity of molasses introduced into the vat, during said last multiplication cycle, (iii) regulating the respective inflows of molasses, nitrogen and $P_2O_5$ such that the yeast harvested at the end of the last multiplication cycle has—

(A) an amount of buds which is less than 5%, and (B) an amount of protein in said yeast corresponding to the optimum activity of the cultivated strain, wherein the optimum activity is the activity which corresponds to the protein content of the yeast for which a higher protein content gives no more than a slight gain in activity and will also cause a definite deterioration in the stability of said yeast, and (C) satisfies the following characteristics:

(a) a trehalose content in the dry matter of at least 12%; p3 (b) a ratio of nitrogen to $P_2O_5$ content of between 2.3 and 3.8; and harvesting the yeast thus cultivated at the end of said last multiplication cycle;

(3) thereafter separating, washing and filtering or compressing the thus-cultivated and harvested yeast so as to obtain a compressed yeast having the characteristic that the supernatant liquid obtained by centrifuging a cream formed of 100 g of said compressed yeast, containing 30–35% of dry matter, and admixing the same with 30 g of demineralized water will exhibit a cryoscopic lowering of at most 0.3° C.

(4) then adding to said thus-obtained compressed yeast an emulsion of an emulsifying agent having an HLB value of between 3 and 11 in water; and (5) finally dividing into fine particles the thus-obtained compressed yeast emulsifying agent composition and drying the same in particulated condition under gentle drying conditions at least sufficient to reduce the water content thereof to the level of a dry matter content of at least 92%, whereby the dried yeast composition thus obtained (a) releases an amount of gas of between 45 ml and 54 ml in test A'$_3$ wherein in said test A'$_3$ 160 mg of dry matter of said dry yeast is rehydrated with 6 ml of distilled water at 38° C. and at the end of 15 minutes of rehydration adding the amount of water, together with 405 mg of NaCl, required to bring the total to 15 ml, to the product resulting from the fifteen minutes rehydration and then adding the resulting yeast/salt/water composition to 20 g of flour, and 2 g of saccharose at 30° C., thereafter kneading the resulting mixture for 40 seconds to obtain a dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and also (b) releases an amount of gas between 23 and 37 ml in test $A'_4$ wherein in said test $A'_4$ the procedure of said test $A'_3$ is followed except that there is added to said flour 5.5 g of saccharose, and the total amount of gas produced is measured after 60 minutes.

9. The process of claim 8, wherein in step (1) the yeast strain selected has the further characteristic of releasing at least 105 ml of gas in two hours in test $A_1$, wherein, in said test $A_1$, the said fresh baker's yeast in an amount corresponding to 160 mg of dry material, and diluted in 15 ml of water containing 27 g of NaCl and 4 g of $(NH_4)_2SO_4$ per liter, is added to 20 g of flour incubated at 30° C. and kneaded for 40 seconds to obtain a dough, maintaining said dough at 30° C. in a vessel for 13 minutes after the beginning of said kneading, thereafter hermetically sealing said vessel and measuring the total amount of gas produced, in ml at 30° C. and 760 mm of Hg, after the expiration of 60 minutes, and then after the expiration of 120 minutes.

10. The process of claim 8, wherein the amount of buds in said step (2)(iii)(A) is less than 1%.

11. The process of claim 8, wherein the weight ratio of culture medium to molasses in step (2)(ii) is between about 3.8 and about 5.

12. The process of claim 8, wherein said discontinuous inflow of molasses in said step (2)(i) is carried out for at least the final 10 hours, and during said time the yeast cell mass multiplies by at least 3.

13. The process according to any one of claims 8, 9, 10, 11 or 12, wherein said emulsifying agent is present in a required amount of between 0.5% and 2% by weight of said yeast composition.

14. An active dried baker's yeast composition prepared according to the process of claim 8.

15. An active dried baker's yeast composition prepared according to the process of claim 9.

16. An active dried baker's yeast composition prepared according to the process of claim 10.

17. A process for preparing a composition in solid particulate form, consisting essentially of an active dry baker's yeast and an emulsifying agent having a HLB value of between 3 and 11 in water and in an amount sufficient to protect said yeast against deterioration during drying, said composition having a dry matter content of at least 92% and having the capability of fermenting sweetened doughs containing more than 5% sugar, said process comprising successively (1) selecting a yeast strain stable to drying and capable of giving a fresh compressed yeast having a gas release of more than 45 ml in a test called $A_3$ wherein in said test $A_3$, the said fresh baker's yeast in an amount corresponding to 160 mg of dry material, and diluted in 15 ml of water containing 27 g of NaCl and 4 g of $(NH_4)_2SO_4$ per liter, is added to 20 g of flour and 2 g of saccharose incubated at 30° C. and kneaded for 40 seconds to obtain a dough, maintaining said dough at 30° C. in a vessel for 13 minutes after the beginning of said kneading, thereafter hermetically sealing said vessel and measuring the total amount of gas produced, in ml at 30° C. and 760 mm of Hg, after the expiration of 60 minutes;

(2) cultivating said yeast strain discontinuously in a plurality of multiplication cycles, having several hours duration each, and carried out in vats previously provided with inoculating yeast and water, by regulated inflows of molasses and other nutrients including nitrogen and $P_2O_5$, harvesting the yeast a the end of each multiplication cycle, and wherein during the last of said multiplication cycles, the cultivation conditions consisting essentially in the combination of:

(i) discontinuous inflow of the molasses during at least the final 10 hours of said last multiplication cycle before harvesting the yeast intended for drying, the said final 10 hours corresponding to a period wherein the cell mass is multiplied by at least 3, (ii) maintaining a value of between about 3.8 and about 5 for the weight ratio of (Culture medium)/(molasses)

wherein "(culture medium)" refers to the entire content of the culture vat including water, yeast and nutrient substances, calculated at the end of the last multiplication cycle and wherein "(molasses)" refers to the total quantity of molasses introduced into the vat, during said last multiplication cycle, (iii) regulating the respective inflows of molasses, nitrogen and $P_2O_5$ such that the yeast harvested at the end of the last multiplication cycle has (A) an amount of buds which is less than 1%, and (B) an amount of protein in said yeast corresponding to the optimum activity of the cultivated strain, wherein the optimum activity is the activity which corresponds to the protein content of the yeast for which a higher protein content gives no more than a slight gain in activity and will also cause a definite deterioration in the stability of said yeast, and (C) satisfies the following characteristics:

(a) a trehalose content in the dry matter of at least 12%;

(b) a ratio of nitrogen to $P_2O_5$ content of between 2.3 and 3.8; and harvesting the yeast thus cultivated at the end of said last multiplication cycle;

(3) thereafter separating, washing and filtering or compressing the thus-cultivated yeast so as to obtain a compressed yeast having the characteristic that the supernatant liquid obtained by centrifuging a cream formed of 100 g of said compressed yeast, containing 30–35% of dry matter, and admixing the same with 30 g of demineralized water will exhibit a cryoscopic lowering of at most 0.3° C.

(4) then adding to said thus-obtained compressed yeast an emulsion of an emulsifying agent having an HLB value of between 3 and 11 in water; and (5) finally dividing into fine particles the thus-obtained compressed yeast emulsifying agent composition and drying the same in particulated condition under gentle drying conditions at least sufficient to reduce the water content thereof to the level of a dry matter content of at least 92%, whereby the dried yeast composition thus obtained (a) releases an amount of gas of between 45 ml and 54 ml in test $A'_3$ wherein in said test $A'_3$ 160 mg of dry matter of said dry yeast is rehydrated with 6 ml of distilled water at 38° C. and at the end of 15 minutes of rehydration adding the amount of water, together with 405 mg of NaCl, required to bring the total to 15 ml, to the product resulting from the fifteen minutes rehydration and then adding the resulting yeast/salt/water composition to 20 g of flour, and 2 g of saccharose at 30° C., thereafter kneading the resulting mixture for 40 seconds to obtain a dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and also (b) releases an amount of gas between 23 and 37 ml in test $A'_4$
  wherein in said test $A'_4$ the procedure of said test $A'_3$ is followed except that there is added to said flour 5.5 g of saccharose, and the total amount of gas produced is measured after 60 minutes.

18. The process according to claim 17, wherein said emulsifying agent is present in a required amount of between 0.5% and 2% by weight of said yeast composition.

19. A process for preparing a yeast composition in solid particulate form, consisting essentially of an active dry baker's yeast and an emulsifying agent having an HLB value of between 3 and 11 in water and in an amount sufficient to protect said yeast against deterioration during drying, said process comprising successively (1) selecting the yeast strain deposited at the N.C.Y.C. under number R 30;
(2) cultivating said yeast strain discontinuously in a plurality of multiplication cycles, having several hours duration each, and carried out in vats previously provided with inoculating yeast and water, by regulated inflows of molasses and other nutrients including nitrogen and $P_2O_5$, harvesting the yeast a the end of each multiplication cycle, and wherein during the last of said multiplication cycles, the cultivation conditions consisting essentially in the combination of:
  (i) maintaining a value of between about 3 and about 7 for the weight ratio of (Culture medium)/(molasses)

wherein "(culture medium)" refers to the entire content of the culture vat including water, yeast and nutrient substances, calculated at the end of the last multiplication cycle and wherein "(molasses)" refers to the total quantity of molasses introduced into the vat, during said last multiplication cycle,
  (ii) regulating the respective inflows of molasses, nitrogen and $P_2O_5$ such that the yeast harvested at the end of the last multiplication cycle has
    (A) an amount of buds which is less than 5%, and
    (B) an amount of protein in said yeast corresponding to the optimum activity of the cultivated strain,
      wherein the optimum activity is the activity which to the protein content of the yeast for which a higher protein content gives no more than a slight gain in activty and will also cause a definite deterioration in the stability of said yeast, and
  (C) the following characteristics:
    (a) a trehalose content in the dry matter of at least 12%;
    (b) a ratio of nitrogen to $P_2O_5$ content of between 2.3 and 3.8; and
  harvesting the yeast thus cultivated at the end of said last multiplication cycle;

(3) thereafter separating, washing and filtering or compressing the thus-cultivated yeast so as to obtain a compressed yeast having the characteristic that the supernatant liquid obtained by centrifuging a cream formed of 100 g of said compressed yeast, containing 30–35% of dry matter, and admixing the same with 30 g of demineralized water will exhibit a cryoscopic lowering of at most 0.3° C.

(4) then adding to said thus-obtained compressed yeast an emulsion of an emulsifying agent having an HLB value of between 3 and 11 in water; and (5) finally dividing into fine particles the thus-obtained compressed yeast emulsifying agent composition and drying the same in particulated condition under gentle drying conditions at least sufficient to reduce the water content thereof to the level of a dry matter content of at least 92%, whereby the dried yeast composition thus obtained
  (a) releases an amount of gas of between 45 ml and 54 ml in test $A'_3$ wherein in said $A'_3$ 160 mg of dry matter of said dry yeast is rehydrated with 6 ml of distilled water at 38° C. and at the end of 15 minutes of rehydration adding the amount of water, together with 405 mg of NaCl, required to bring the total to 15 ml, to the product resulting from the fifteen minutes rehydration and then adding the resulting yeast/salt/water composition to 20 g of flour, and 2 g of saccharose at 30° C., thereafter kneading the resulting mixture for 40 seconds to obtain a dough, maintaining said dough at 30° C. in a vessel for 13 minutes after the beginning of said kneading, thereafter hermetically sealing said vessel and measuring the total amount of gas produced, in ml, at 30° C. and 760 mm of Hg, after the expiration of 60 minutes; and also (b) releases an amount of gas between 23 and 37 ml in test $A'_4$
    wherein in said test $A'_4$ the procedure of said test $A'_3$ is followed except that there is added to said flour 5.5 g of saccharose, and the total amount of gas produced is measured after 60 minutes.

20. The process according to claim 19 wherein the regulation of the respective inflows of molasses, nitrogen and $P_2O_5$ is such that the yeast harvested at the end of the last multiplication cycle has an amount of buds which is less than 1%.

21. The process according to any one of claims 8, 17, 19 or 20, wherein in said step (5) the said gentle drying conditions are at least sufficient to reduce the water content thereof to the level of a dry matter content between 94% and 97%.

22. An active dried baker's yeast composition prepared according to the process of claim 19.

23. A bread-making dough product containing at least 5% sugar in its constituent formula and an active dried baker's yeast composition according to any one of claims 14, 15, 16 or 22.

* * * * *